United States Patent [19]

Rajagopalan et al.

[11] Patent Number: 5,162,109
[45] Date of Patent: Nov. 10, 1992

[54] MAGNETIC RESONANCE IMAGING AGENTS

[75] Inventors: Raghavan Rajagopalan, Maryland Heights; Donald R. VanDeripe, Lake St. Louis, both of Mo.

[73] Assignee: Mallinckrodt Medical, Inc., St. Louis, Mo.

[21] Appl. No.: 581,861

[22] Filed: Sep. 13, 1990

[51] Int. Cl.⁵ ............................................. A61K 49/00
[52] U.S. Cl. ..................................... 424/1.1; 534/15; 534/16
[58] Field of Search ................... 424/1.1; 534/15, 16; 556/44, 50, 55, 56, 62, 63, 115, 116, 136, 148; 514/502, 505, 499, 501, 740

[56] References Cited

U.S. PATENT DOCUMENTS

| | | | |
|---|---|---|---|
| 4,687,659 | 8/1987 | Quay | 424/9 |
| 4,826,673 | 5/1989 | Dean et al. | 424/9 |
| 5,037,631 | 8/1991 | Nosco | 424/1.1 |

*Primary Examiner*—Robert L. Stoll
*Assistant Examiner*—C. Sayala
*Attorney, Agent, or Firm*—Evan R. Witt

[57] ABSTRACT

A diagnostic composition suitable for administration to a warm-blooded animal, which comprises a MRI-effective amount of a zwitterionic complex of a paramagnetic ion having a cyclic or open chain structure and a pharmaceutically acceptable carrier and a method for performing a MRI diagnostic procedure using the same.

5 Claims, No Drawings

MAGNETIC RESONANCE IMAGING AGENTS

BACKGROUND OF THE INVENTION

This invention relates to magnetic resonance imaging (MRI) agents and, more particularly, to methods and compositions for enhancing MRI.

The recently developed technique of MRI encompasses the detection of certain atomic nuclei utilizing magnetic fields and radio-frequency radiation. It is similar in some respects to X-ray computed tomography (CT) in providing a cross-sectional display of the body organ anatomy with excellent resolution of soft tissue detail. As currently used, the images produced constitute a map of the proton density distribution and/or the relaxation times in organs and tissues. The technique of MRI is advantageously non-invasive as it avoids the use of ionizing radiation.

While the phenomenon of MRI was discovered in 1945, it is only relatively recently that it has found application as a means of mapping the internal structure of the body as a result of the original suggestion of Lauterbur (Nature, 242, 190-191 [1973]). The fundamental lack of any known hazard associated with the level of the magnetic and radio-frequency fields that are employed renders it possible to make repeated scans on vulnerable individuals. In addition to standard scan planes (axial, coronal, and sagittal), oblique scan planes can also be selected.

In a MRI experiment, the nuclei under study in a sample (e.g. protons) are irradiated with the appropriate radio-frequency (RF) energy in a highly uniform magnetic field. These nuclei, as they relax, subsequently emit RF at a sharp resonance frequency. The resonance frequency of the nuclei depends on the applied magnetic field.

According to known principles, nuclei with appropriate spin, when placed in an applied magnetic field (B, expressed generally in units of gauss or Tesla [$10^4$ gauss]) align in the direction of the field. In the case of protons, these nuclei precess at a frequency, f, of 42.6 MHz, at a field strength of 1 Tesla. At this frequency, an RF pulse of radiation will excite the nuclei and can be considered to tip the net magnetization out of the field direction, the extent of this rotation being determined by the pulse duration and energy. After the RF pulse, the nuclei "relax" or return to equilibrium with the magnetic field, emitting radiation at the resonant frequency. The decay of the emitted radiation is characterized by two relaxation times, i.e., $T_1$, the spin-lattice relaxation time or longitudinal relaxation time, that is, the time taken by the nuclei to return to equilibrium along the direction of the externally applied magnetic field, and $T_2$, the spin-spin relaxation time associated with the dephasing of the initially coherent precession of individual proton spins. These relaxation times have been established for various fluids, organs and tissues in different species of mammals.

In MRI, scanning planes and slice thicknesses can be selected. This selection permits high quality transverse, coronal and sagittal images to be obtained directly. The absence of any moving parts in MRI equipment promotes high reliability. It is believed that MRI has a greater potential than CT for the selective examination of tissue characteristics in view of the fact that in CT, X-ray attenuation coefficients alone determine image contrast, whereas at least five separate variables ($T_1$, $T_2$, proton density, pulse sequence and flow) may contribute to the MRI signal. For example, it has been shown (Damadian, Science, 171, 1151 [1971]) that the values of the $T_1$ and $T_2$ relaxation in tissues are generally longer by about a factor of two (2) in excised specimens of neoplastic tissue compared with the host tissue.

By reason of its sensitivity to subtle physicochemical differences between organs and/or tissues, it is believed that MRI may be capable of differentiating different tissue types and in detecting diseases which induce physicochemical changes that may not be detected by X-ray or CT which are only sensitive to differences in the electron density of tissue.

As noted above, two of the principal imaging parameters are the relaxation times, $T_1$ and $T_2$. For protons (or other appropriate nuclei), these relaxation times are influenced by the environment of the nuclei, (e.g., viscosity, temperature, and the like). These two relaxation phenomena are essentially mechanisms whereby the initially imparted radio-frequency energy is dissipated to the surrounding environment. The rate of this energy loss or relaxation can be influenced by certain other nuclei which are paramagnetic. Chemical compounds incorporating these paramagnetic nuclei may substantially alter the $T_1$ and $T_2$ values for nearby protons. The extent of the paramagnetic effect of a given chemical compound is a function of the environment within which it finds itself.

In general, paramagnetic divalent or trivalent ions of elements with atomic numbers of 21 to 29, 42 to 44 and 58 to 70 have been found effective as MRI image contrasting agents. Suitable such ions include chromium (III), manganese (II), manganese (III), iron (II), iron (III), cobalt (II), nickel (II), copper (II), praseodymium (III), neodymium (III), samarium (III), and ytterbium (III). Because of their very strong magnetic moments, gadolinium (III), terbium (III), dysprosium (III), holmium (III) and erbium (III) are preferred. Gadolinium (III) ions have been particularly preferred as MRI contrasting agents.

Typically, the divalent and trivalent paramagnetic ions have been administered in the form of complexes with organic complexing agents. Such complexes provide the paramagnetic ions in a soluble, non-toxic form, and facilitate their rapid clearence from the body following the imaging procedure. Gries et al., U.S. Pat. No. 4,647,447, disclose complexes of various paramagnetic ions with conventional aminocarboxylic acid complexing agents. A preferred complex disclosed by Gries et al. is the complex of gadolinium (III) with diethylene-triamine-pentaacetic acid ("DTPA") represented by the formula:

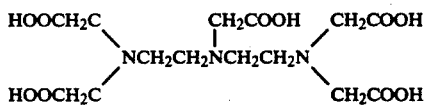

Paramagnetic ions, such as gadolinium (III), have been found to form strong complexes with DTPA, ethylenediamine-tetraacetic acid ("EDTA") represented by the formula:

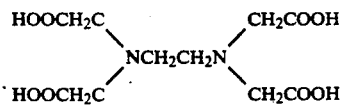

and with tetraazacyclododecane-N,N',N", N'"-tetraacetic acid ("DOTA") represented by the formula:

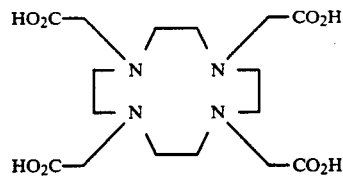

These complexes do not dissociate substantially in physiological aqueous fluids. The gadolinium complex of DTPA has a net charge of −2, whereas the gadolinium complex of EDTA and DOTA has a net charge of −1, and both are generally administered as soluble salts. Typical such salts are sodium and N-methylglucamine. The administration of such salts is attended by certain disadvantages. These salts can raise the in vivo ion concentration and cause localized disturbances in osmolality, which in turn, can lead to edema and other undesirable reactions.

Efforts have been made to design new ionic and neutral paramagnetic metal complexes which avoid or minimize the above mentioned disadvantages. In general, this goal can be achieved by converting one or more of the free carboxylic acid groups of the complexing agent to neutral, non-ionizable groups. For example, S. C. Quay, in U.S. Pat. Nos. 4,687,658 and 4,687,659, discloses alkylester and alkylamide derivatives, respectively, of DTPA complexes. Similarly, published Dean et al., U.S. Pat. No. 4,826,673 discloses mono- and polyhydroxyalkylamide derivatives of DTPA and their use as complexing agents for paramagnetic ions. It can also be achieved by covalent attachment of organic cations to the complexing agent in such a manner that the sum of positive and negative charges in the resulting metal complex is zero.

The nature of additional substituents in the complexing agent can have a significant impact on tissue specificity. Hydrophilic complexes tend to concentrate in the interstitial fluids, whereas lipophilic complexes tend to associate with cells. Thus, differences in hydrophilicity can lead to different applications of the compounds. See, for example, Weinmann et al., *AJR*, 142, 679 (Mar. 1984) and Brasch, et al., *AJR*, 142, 625 (Mar. 1984).

Thus, a need continues to exist for new and structurally diverse ionic and neutral complexes of paramagnetic ions for use as MRI agents. There is further a need in the art to develop highly stable complexes with good relaxivity and osmolar characteristics.

SUMMARY OF THE INVENTION

The present invention provides novel complexing agents and complexes of complexing agents with paramagnetic ions. The resulting metal complexes have net zero charges and are referred to as "zwitterionic complexes". The zwitterionic complexes are preferably of paramagnetic metal ions of atomic number 21–29, 42–44, 58–70 along with a suitable complexing agent such that the total number of positive and negative charges contributed by the metal ion and the complexing agent is equal. Such complexes are illustrated in the following formulas.

A zwitterionic complex having a cyclic structure is illustrated in formula 1:

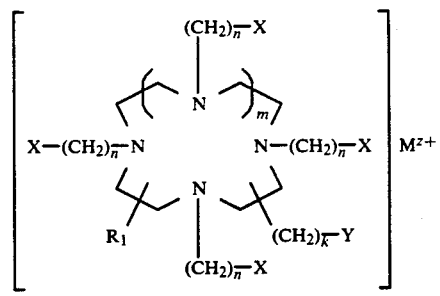

wherein $R_1$ is selected from a group consisting of hydrogen, alkyl—such as for example methyl or ethyl wherein methyl is preferable to reduce lipophilicity, aryl—such as for example phenyl, acyl such as for example acetyl, mono- or poly- hydroxyalkyl—such as for example hydroxymethyl or dihydroxypropyl wherein dihydroxypropyl is preferable to enhance water solubility, mono- or poly- alkoxyalkyl—such as for example methoxyethyl or dimethoxymethyl wherein dimethoxymethyl is preferred to reduce lipophilicity, and acylaminoalkyl—such as for example acetylaminomethyl or proprionylaminomethyl; n ranges from 1 to 6, but most preferably 1; m ranges from 0 to 2, but most preferably 0 or 1; k ranges from 0 to 10, but most preferably 1; $M^{z+}$ is a paramagnetic ion of an element having a valence, z, of 2+, 3+, or 4+, but most preferably 2+ or 3+; x is an anionic group selected from the group consisting of carboxylate, sulfonate, phosphonate, phosphate, hydrogen phosphonate, and hydrogen phosphate; and y is a cationic group selected from the group consisting of ammonium, phosphonium, and sulfonium. The individual charges of x, y and z as defined above are selected such that their sum total charge in the paramagnetic metal complex is always 0. For example, if the paramagnetic metal is gadolinium, x is a carboxylate anion, and y is an ammonium cation, then the zwitterionic complex would have z=3+, (4)x=−4, and y=1+, having the net overall charge of 0.

Another zwitterionic complex having an open chain structure is illustrated in formula 2:

FORMULA 2

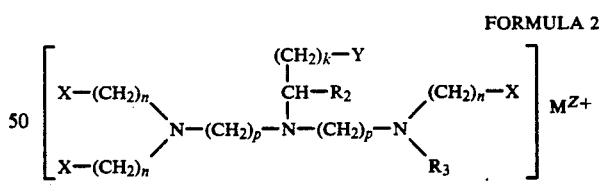

wherein $R_2$ is selected from a group consisting of hydrogen, alkyl—such as for example methyl or ethyl wherein methyl is preferable to reduce lipophilicity, aryl—such as for example phenyl, acyl—such as for example acetyl, mono- or poly- hydroxyalkyl—such as for example hydroxymethyl or dihydroxypropyl wherein dihydroxypropyl is preferable to enhance water solubility, mono- or poly- alkoxyalkyl—such as for example methoxyethyl or dimethoxymethyl wherein dimethoxymethyl is preferred to reduce lipophilicity and acylaminoalkyl—such as for example acetylaminomethyl or proprionylaminomethyl; x is the same as that defined in formula 1 above; y is the same as that defined in formula 1 above; n is the same as that defined in formula 1 above; and the p groups may be same or different ranging from 2 to 5, but most preferably 2; $R_3$ is selected from a group consisting of hydrogen, alkyl—such as for example methyl or ethyl wherein methyl is preferable to reduce lipophilicity, aryl—such as for example phenyl, acyl—such as for example acetyl, mono- or poly- hydroxyalkyl—such as for example hydroxymethyl or dihydroxypropyl wherein dihydroxypropyl is preferable to enhance water solubility, mono- or poly- alkoxyalkyl—such as for example methoxyethyl or dimethoxymethyl wherein dimethoxymethyl is preferred to reduce lipophilicity, acylaminoalkyl—such as for example acetylaminomethyl or proprionylaminomethyl and —$(CH_2)_n$—X depending on the valency of the paramagnetic ion; and k is the same as that defined in formula 1 above, but most preferably 0; and $M^{z+}$ is a paramagnetic ion of an element having a valence, z, as defined in formula 1 above. The charges of x, y and z in formula 2 are likewise selected so that their sum total charge is 0 in the paramagnetic metal complex. For example, if the metal ion is gadolinium, x is a carboxylate anion and y is an ammonium cation, then the zwitterionic complex derived from formula 2 would have $z=3+$, $(4)x=-4$ and $y=1+$ for an overall sum total charge of 0. If the metal ion is manganese, then $z=2+$, $(3)x=-3$, $y=1+$ for an overall sum total charge of 0.

Other zwitterionic complexes of the present invention are represented by the following cyclic structural formula 3:

FORMULA 3

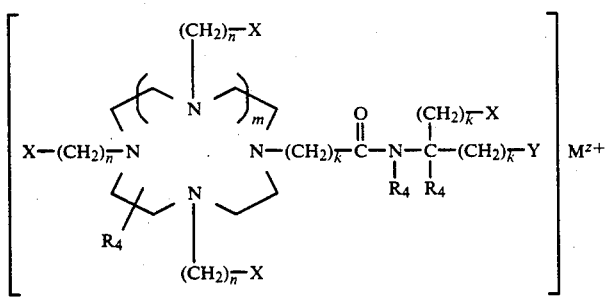

wherein the $R_4$ groups may be the same or different selected from a group consisting of hydrogen, alkyl—such as for example methyl or ethyl wherein methyl is preferable to reduce lipophilicity, aryl—such as for example phenyl, acyl—such as for example acetyl, mono- or poly- hydroxyalkyl—such as for example hydroxymethyl or dihydroxypropyl wherein dihydroxypropyl is preferable to enhance water solubility, mono- or poly- alkoxyalkyl—such as for example methoxyethyl or dimethoxymethyl wherein dimethoxymethyl is preferred to reduce lipophilicity and acylaminoalkyl—such as for example acetylaminomethyl or proprionylaminomethyl; and x, y, z, n, m and k are the same, respectively, as those defined in formula 1; and by the open chain structural formula 4:

wherein $R_5$ is selected from a group consisting of hydrogen, alkyl—such as for example methyl or ethyl wherein methyl is preferable to reduce lipophilicity, aryl—such as for example phenyl, acyl—such as for example acetyl, mono- or poly- hydroxyalkyl—such as for example hydroxymethyl or dihydroxypropyl wherein dihydroxypropyl is preferable to enhance water solubility, mono- or poly- alkoxyalkyl—such as for example methoxyethyl or dimethoxymethyl wherein dimethoxymethyl is preferred to reduce lipophilicity and acylaminoalkyl—such as for example acetylaminomethyl or proprionylaminomethyl; x, y, z, n, m and k are the same, respectively, as those defined in formula 1 above; and t ranges from 2 to 10; whereby k and t may be the same or different, but preferably k is 1 and t is 2.

Still another zwitterionic complex of the present invention is represented by the following open chain formula 5:

FORMULA 5

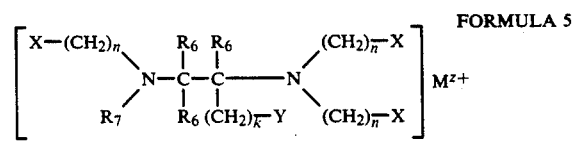

wherein the $R_6$ groups may be the same or different selected from a group consisting of hydrogen, alkyl—such as for example methyl or ethyl wherein methyl is preferable to reduce lipophilicity, aryl—such as for example phenyl, acyl—such as for example acetyl, mono- or poly- hydroxyalkyl—such as for example hydroxymethyl or dihydroxypropyl wherein dihydroxypropyl is preferable to enhance water solubility, mono- or poly- alkoxyalkyl—such as for example methoxyethyl or dimethoxymethyl wherein dimethoxymethyl is preferred to reduce lipophilicity and acylaminoalkyl—such as for example acetylaminomethyl or proprionylaminomethyl; x, y, z, n and k are the same, respectively, as those defined in formula 1 above; and $R_7$ is selected from a group consisting of hydrogen, alkyl—such as for example methyl or ethyl wherein methyl is preferable to reduce lipophilicity, aryl—such

FORMULA 4

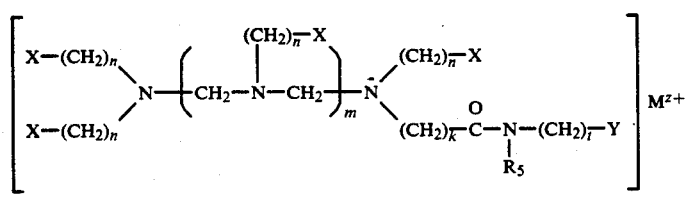

as for example phenyl, acyl—such as for example acetyl, hydroxy, alkoxyl—such as for example methoxy or ethoxy, mono- or poly- hydroxyalkyl —such as for example hydroxymethyl or dihydroxypropyl wherein dihydroxypropyl is preferable to enhance water solubility, mono- or poly- alkoxyalkyl—such as for example methoxyethyl or dimethoxymethyl wherein dimethoxymethyl is preferred to reduce lipophilicity, acylaminoalkyl—such as for example acetylaminomethyl or proprionylaminomethyl, and —$(CH_2)_n$—X.

In all five formulas defined above, preferred compounds are produced when the substituted alkyl, alkoxyl, aryl, acyl, mono- or poly- hydroxyalkyl, mono- or poly-alkoxyalkyl and acylaminoalkyl groups contain from 1 to 10 carbon atoms but more preferably from 2 to 7 carbon atoms.

DESCRIPTION OF THE PREFERRED EMBODIMENTS

In accordance with the present invention, the compounds of Formulas 1-5 are considered to be suitable for use as magnetic resonance imaging (MRI) agents. These agents are prepared by a multi-step process illustrated in the examples below and may be used in various radiographic procedures including those involving cardiography, coronary arteriography, aortography, cerebral and perepheral angiography, arthography, intravenous pyelography and urography. In further accordance with the present invention, pharmaceutical compositions may be prepared containing the aforementioned compounds of the present invention as a magnetic resonance imaging agent together with a pharmaceutically acceptable carrier.

A pharmaceutical composition so prepared is used in a method of performing a MRI diagnostic procedure which involves administering enterally or parenterally to a warm-blooded animal an effective amount of the compound of the present invention and a pharmaceutically acceptable carrier and excipients which would be appropriate for the procedure and then exposing the warm-blooded animal to a MRI procedure, thereby imaging at least a portion of the body of the warm-blooded animal. Such solutions may also contain pharmaceutically acceptable buffers and, optionally, electrolytes such as sodium chloride. Advantageously, the compositions may further contain physiologically acceptable non-toxic cations in the form of a gluconate, chloride or other suitable organic or inorganic salts, including suitable soluble complexes with a chelate/ligand to enhance safety. Such physiologically acceptable, non-toxic cations include calcium ions, magnesium ions, copper ions, zinc ions and the like including mixtures thereto. Calcium ions are preferred.

Pharmaceutically acceptable carriers include those that are suitable for injection such as aqueous buffer solutions, e.g. tris(hydroxymethyl)aminomethane (and its salts), phosphate, citrate, bicarbonate, etc., sterile water for injection, physiological saline, and balanced ionic solutions containing chloride and/or bicarbonate salts of normal blood plasma cations such as Ca, Na, K and Mg. Other buffer solutions are described in Remington's *Practice of Pharmacy*, Eleventh Edition, for example on page 170. The carriers may contain a chelating agent, e.g. a small amount of ethylenediaminetetraacetic acid, calcium disodium salt or other pharmaceutically acceptable chelating agents.

Parenteral compositions may be injected directly or mixed with a large volume parenteral composition for systemic administration.

Formulations for enteral administration may vary widely, as is well-known in the art. In general, such formulations are liquids which include an effective amount of the paramagnetic ion complex in aqueous solution or suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement of the magnetic resonance image. Such doses may vary widely, depending upon the particular zwitterionic compound employed, the organs or tissues which are the subject of the imaging procedure, the MRI equipment being used, etc. In general, parenteral dosages will range from about 0.01 to about 1.0 MMol of zwitterionic compound per kg of patient body weight. Preferred parenteral dosages range from about 0.05 to about 0.5 MMol of zwitterionic compound per kg of patient body weight. Enteral dosages generally range from about 0.5 to about 100 MMol, preferably from about 1.0 to about 20 MMol of zwitterionic compound per kg of patient body weight.

The novel MRI contrasting agents of this invention possess a unique combination of desirable features. The compounds exhibit a high solubility in physiological fluids. This high solubility allows the preparation of concentrated solutions, thus minimizing the amount of fluid required to be administered. The zwitterionic characteristic of the compounds also reduces the osmolarity of the diagnostic compositions, thus preventing undesired edema and other side effects.

The diagnostic compositions of this invention are used in the conventional manner. The compositions may be administered in a sufficient amount to provide adequate visualization to a warm-blooded animal either systemically or locally to the organ or tissue to be imaged, and the animal then scanned with a suitable MRI machine. The zwitterionic compound of the present invention is administered to the warm-blooded animal so that the compound remains in the living animal body for about 2 to 3 hours, although shorter and longer residence periods are normally acceptable. The compositions have been found to enhance the magnetic resonance images obtained by these procedures.

The invention is further illustrated by the following examples, which are not intended to be limiting.

EXAMPLE I

Preparation of Aminopentyl-EDTA (6)

A. Preparation of 5.6-Diazido-1-cyanohexane(2)

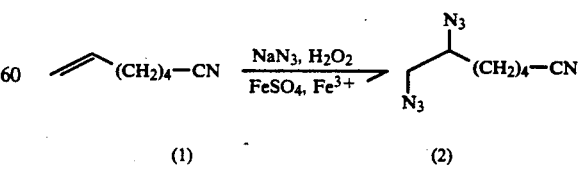

Solid $NaN_3$ (0.8 g, 0.12 mol) was dissolved in 30 ml of water and placed in a one liter 3-neck flask prior to adding 40 ml of $CH_3OH$ for dilution. The diluted solution was then placed in an ice bath and cooled to 0° C.

Neat 6-cyano-1-hexene (4.36 g, 0.04 mol) was then added to the diluted solution, followed by the addition of $Fe_2(SO_4)_3$ (0.8 g, 0.002 mol). The mixture was again cooled to 0° C.

Solid $FeSO_4$ (24 g, 0.08 mol) was then dissolved in 75 ml of water and placed in an addition funnel. Ice cold $H_2O_2$ (30%) was also placed in a separate addition funnel and kept cold.

The $FeSO_4$ solution was added to the diluted solution in approximately 5 ml aliquots while the peroxide was added dropwise while maintaining the temperature of the solution at approximately 0° C. After the addition of the $FeSO_4$ solution and peroxide was completed, the reaction mixture was stirred for approximately 15 minutes whereby TLC showed a complete disappearance of the starting material.

The reaction mixture was then diluted with 200 ml water and extracted four times with 100 ml portions of $CH_2Cl_2$.

The organic layer was washed with water, dried and evaporated to give 5,6-Diazido-1-cyanohexane (5.3 g; 68% yield) which was used as such immediately since the diazide develops color after leaving overnight.

B. Preparation of 6,7-Diaminoheptanenitrile(3)

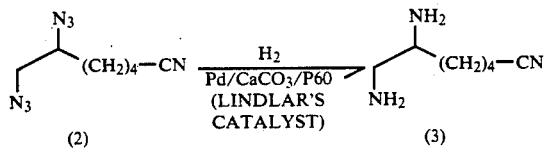

A solution of 5,6-diazido-1-cyanohexane (5.2 g, 0.026 mol) in $CH_3OH$ (50 ml) was hydrogenated at 30 pounds of pressure over Lindlar's Catalyst (7 g) for 12 hours.

The solution was then filtered through celite and 4 g of fresh Lindlar's Catalyst was added. The solution was then hydrogenated at 30 pounds for approximately 12 hours.

The solvent was then evaporated and the residue was distilled under reduced pressure at 100°-110° C. (Krugelrohr) to give 6,7-Diaminoheptanenitrile as a colorless oil (2 g, 48% yield). The IR showed no loss of the —CN group.

C. Preparation of 6,7-[N,N,N',N'-tetracarboxymethylamino]heptanenitrile(5)

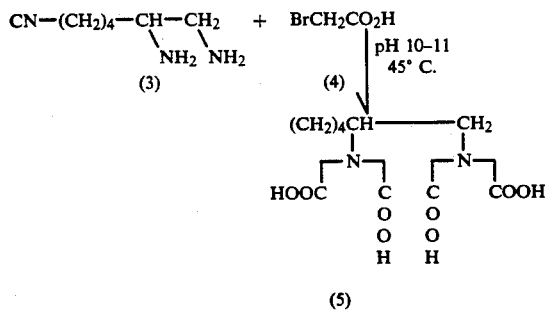

To a solution of bromoacetic acid (5.9 g, 0.0423 mol) in 11 ml of water was added a NaOH solution (3.4 g in 17 ml of $H_2O$) to adjust the pH to approximately 7 or 7.5.

Neat 6,7-diaminoheptanenitrile (1.41 g, 0.01 mol) was then added in one lot and the mixture was heated to 45° C. The pH was maintained between 10 and 11 with the NaOH solution prepared above.

The pH began to stabilize in approximately 3 hours. The remaining NaOH solution prepared above was added to the mixture and stirred at room temperature (25° C.) for 2 days.

The filtrate was then evaporated to dryness and the residue was dissolved in 20 ml of water and 100 ml methanol.

The solution was then treated with BIO-RAD ion exchange resin (FORMATE FORM) to remove the bromide ions.

After filtration and evaporation of the solution, the residue was treated with hot methanol (100 ml). The precipitate was then filtered through a Buchner funnel and dried to give 2 g (50% yield) of colorless solid m.p. (275°-280° C.). Both the nuclear magnetic resonance (NMR) spectra and elemental analysis were consistent with the structure.

D. Preparation of a Aminopentyl-EDTA (6)

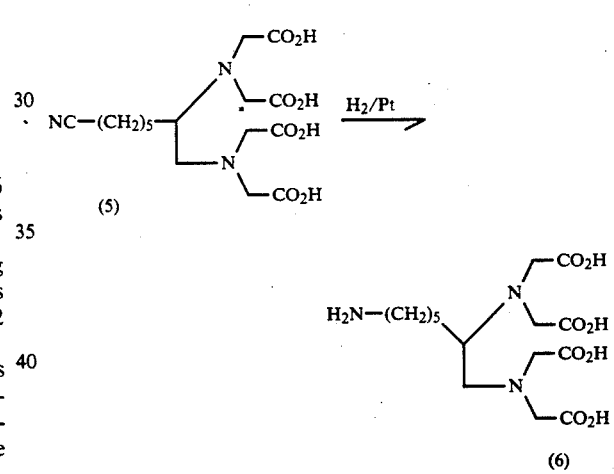

Solid 6,7-[N,N,N', N',-tetracarboxymethylamino]-heptanenitrile (1.5 g, $4 \times 10^{-3}$ mol) was dissolved in $CH_3CO_2H$ and hydrogenated at 3 atm of pressure (45 psi) for 24 hours.

The catalyst $PtO_2$ (400 mg was filtered off of the solution and the filtrate then evaporated to dryness.

Purification of the crude material by ion-exchange resin (BIO-RAD-formate form, AG 1×8, 200–400 mesh) procured 610 mg of the pure compound.

EXAMPLE II

Preparation of the gadolinium complex of aminopentyl-EDTA (7)

A mixture of the ligand (0.5 g) and gadolinium oxide (0.22 g) in water (5 ml) was heated at 65°-70° C. for 20 hours. The pH was adjusted to 7.0 with 1N NaOH and the pale yellow solution was treated with charcoal (1 g), and filtered. The filtrate was then evaporated slowly to obtain a white solid.

EXAMPLE III

Preparation of
[((7-aminoheptyl)imino)bisethylenenitrilo)]tetraacetic acid (14)

A. Preparation of (6-cyanohexyl)bis(2-phthalimidoethyl)amine (10)

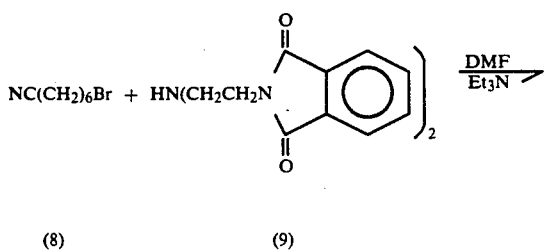

(8)  (9)

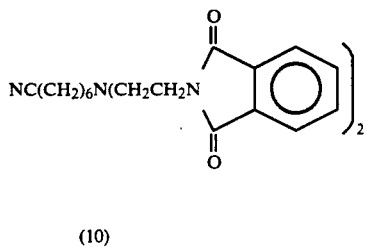

(10)

A mixture of 6-bromohexylcyanide (1) (13.88 g, 0.073 mol), bis(2-phthalimidoethyl)amine (2) (26.52 g, 0.073 mol), and triethylamine (7.37 g, 0.073 mol) in DMF (120 ml) was heated at 100° C. for 20 hours.

After cooling, the precipitate which had formed was removed by filtration and the filtrate was poured into ice (1000 ml). The aqueous solution was extracted with dichloromethane (3×200 ml) and the combined organic extracts were then washed with brine and dried over $Na_2SO_4$.

Removal of the solvent under reduced pressure gave crude product (10) which was flash chromatographed on silica gel (hexanes - 30% ethyl acetate/hexanes gradient elution). Impure fractions were rechromatographed to provide a total of 14.1 g of (10) (41%) as an oil.

The product showed as only one spot on TLC and the IR and NMR Spectra were consistent with the assigned structure (10).

B. Preparation of (6-cyanohexyl)bis(2-aminoethyl)amine (12)

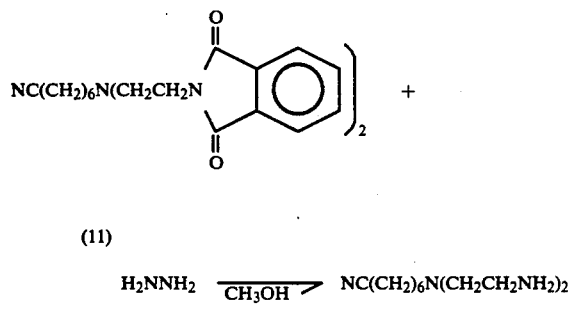

(11)

$H_2NNH_2$ $\xrightarrow{CH_3OH}$ $NC(CH_2)_6N(CH_2CH_2NH_2)_2$ (12)

A solution of the amine (3) (13.8 g, 0.029 mol) and hydrazine (2.15 g, 0.067 mol) in methanol (150 ml) was refluxed for 1.5 hours and allowed to stand overnight. The solvent was removed under reduced pressure and the residue was taken up in water (200 ml) and brought to pH 2 with HCl.

The precipitate was removed by filtration and the filtrate was made basic with solid NaOH. The solution was then concentrated under reduced pressure and extracted with dichloromethane (4×50 ml).

The combined organic extracts were dried over $Na_2SO_4$ and evaporated under reduced pressure. Kugelrohr distillation of the residue gave pure (4) as a water white liquid (4.1 g - 67%) collected between 120° and 140° C. (pot temp) at 0.07 mm Hg. The IR and NMR Spectra were consistent with the assigned structure.

Preparation of
[((6-cyanohexyl)imino)-bis(ethylenenitrilo)]-tetraacetic acid (5)

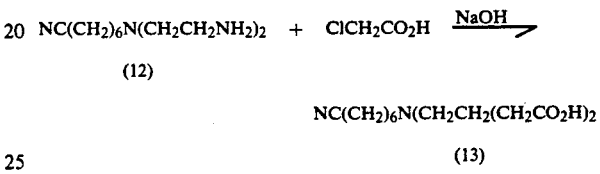

(12)

$NC(CH_2)_6N(CH_2CH_2(CH_2CO_2H)_2$ (13)

A solution of chloroacetic acid (7.0 g, 0.074 mol) in water (20 ml) was neutralized by addition of the required amount of a solution of sodium hydroxide (5.92 g, 0.148 mol) in water (30 ml).

The diamine (4) (3.72 g, 0.0175 mol) was added and the solution was heated at 45° C. for seven hours. During this time the pH of the solution was kept between 10 and 11 through addition of the remaining NaOH solution.

After stirring at room temperature for two days the solution was brought to pH 7 with concentrated HCl and the solvent was removed under reduced pressure. The residue was taken up in hot methanol (300 ml) and filtered.

Removal of the methanol under reduced pressure gave the crude tetraacid (5). This material was chromatographed in 2 gram batches on a 2×30 cm column of BioRad AG 1×8 ion exchange resin in the formate form (gradient elution, 0-1M formic acid) to provide a total of 4.3 g (55%) of the tetraacid (5).

The product showed as only one spot on TLC (ethanol, 7% aqNH$_3$, 4:1, - silica plate). The carbon NMR spectrum (C-176) was consistent with the assigned structure (5).

D. Preparation of [((7-aminoheptyl)imino)bis(ethylenenitrilo)]tetraacetic acid (6)

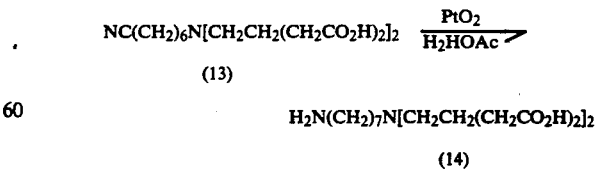

(13)

$H_2N(CH_2)_7N[CH_2CH_2(CH_2CO_2H)_2]_2$ (14)

A solution of the nitrile (5) (0.85 g, 0.0019 mol) in acetic acid (50 ml) was treated with platinum oxide (0.15 g) and hydrogenated at 45 psi overnight.

The catalyst was then removed by filtration through celite and the filter pad was rinsed with water.

The solvent was removed under reduced pressure to yield crude product, which was chromatographed on a BioRad AG 1×8 ion exchange resin in the formate form. Elution with water gave pure (6) (0.70 g, 82%). The product showed as only one spot on the TLC. The proton and carbon NMR spectrum were consistent with structure (6).

EXAMPLE IV

A. Preparation of 1-(6-amino-6-carboxyhexyl)carbamoylmethyl-1,4,7,10-tetraaza-4,7,10-tris(carboxymethyl)cyclododecane (15)

The lysine derivative of DOTA (15) can be synthesized by using methods reported by Krejcarck and Tucker which may be found in *Biochem. Biophys. Res. Commun.* 1977,77,581, with only minor modifications.

In a typical synthesis, the free-acid form of DOTA (0.17 g, 0.29 mmol) and triethylamine (1.15 mmol) dissolve in dry DMSO (15 mL) with gentle warming. The resulting clear solution is cooled to room temperature, and isobutyl chloroformate (0.29 mmol) is added dropwise, followed by addition of an excess (2.07 mmol) of 6-amino-2-(N-benzyloxycarboxyl)aminocaproic acid.

The carbobenzyloxy group (CBZ) is then removed by catalytic hydrogenation.

The resulting mixture is stirred for 30 minutes and then filtered. The DMSO present is then distilled off under vacuum.

In view of the above, the several objects of this invention are achieved.

As various changes could be made in the above compounds, and methods without departing from the scope of the invention, it is intended that all matter contained in the above description or shown in the accompanying drawings shall be interpreted as illustrative and not in a limiting sense.

What is claimed is:

1. A zwitterionic complex comprising the following straight chain structural formula 2,

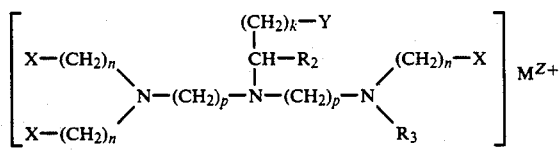

wherein $R_2$ is selected from a group consisting of hydrogen, alkyl, aryl, acyl, mono- or poly-hydroxyalkyl, mono- or poly-alkoxyalkyl and acylaminoalkyl; $R_3$ may be the same as $R_2$ or can be $-(CH_2)_n-X$; X is an anionic group selected from the group consisting of carboxylate, sulfonate, phosphonate, hydrogen phosphonate, phosphate and hydrogen phosphate; Y is a cationic group selected from a group consisting of ammonium, phosphonium, and sulfonium; $M^{z+}$ is a paramagnetic ion having a valence, Z, of 2+, 3+ or 4+; n ranges from 1 to 6; k ranges from 0 to 10; and p ranges from 2 to 5.

2. A zwitterionic complex as set forth in claim 1 wherein said paramagnetic ion is $Gd^{3+}$, $Dy^{3+}$, $Fe^{3+}$, or $Mn^{2+}$.

3. A diagnostic composition suitable for administration to a warm-blooded animal, which comprises a MRI-effective amount of a zwitterionic complex of paramagnetic ions of atomic number 21-29, 42-44, or 58-70 having the straight chain structural formula 2,

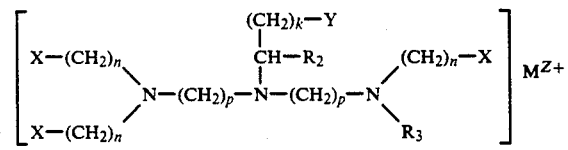

wherein $R_2$ is selected from a group consisting of hydrogen, alkyl, aryl, acyl, mono- or poly-hydroxyalkyl, mono- or poly-alkoxyalkyl and acylaminoalkyl; $R_3$ may be the same as $R_2$ or can be $-(CH_2)_n-X$; X is an anionic group selected from the group consisting of carboxylate, sulfonate, phosphonate, hydrogen phosphonate, phosphate and hydrogen phosphate; Y is a cationic group selected from a group consisting of ammonium, phosphonium, and sulfonium; $M^{z+}$ is a paramagnetic ion having a valence, Z, of 2+, 3+ or 4+; n ranges from 1 to 6; k ranges from 0 to 10; and p ranges from 2 to 5, and a pharmaceutically acceptable carrier.

4. The diagnostic composition as set forth in claim 3 wherein said paramagnetic ion is $Gd^{3+}$, $Dy^{3+}$, $Fe^{3+}$, or $Mn^{2+}$.

5. The diagnostic composition suitable for administration to a warm-blooded animal as set forth in claim 3 wherein the total number of positive and negative valences contributed by the carrier and the chelated paramagnetic ions is equal.

* * * * *